United States Patent [19]
Greenawalt

[11] Patent Number: 5,787,608
[45] Date of Patent: Aug. 4, 1998

[54] CUSTOM-MADE FOOTWEAR

[76] Inventor: Kent S. Greenawalt, 5056 Hunting Hills Sq., Roanoke, Va. 24014

[21] Appl. No.: 688,617

[22] Filed: Jul. 30, 1996

[51] Int. Cl.⁶ .................................. A61F 5/14; A43B 7/14
[52] U.S. Cl. ........................ 36/11.5; 36/140; 36/88; 36/91; 36/169
[58] Field of Search ......................... 36/11.5, 88, 91, 36/140, 37, 145, 161, 166, 169, 180, 29

[56] References Cited

U.S. PATENT DOCUMENTS

| | | | |
|---|---|---|---|
| 2,146,805 | 2/1939 | Engel | 36/11.5 |
| 2,167,035 | 7/1939 | Westheimer | 36/11.5 |
| 2,367,232 | 1/1945 | Marx | 36/11.5 |
| 2,502,774 | 4/1950 | Alianiello | 36/37 |
| 2,586,057 | 8/1952 | Knellwolf | |
| 2,772,488 | 12/1956 | Meltzer | 36/37 |
| 2,863,231 | 12/1958 | Jones | 36/37 |
| 2,865,097 | 12/1958 | Vollrath, Jr. | |
| 2,932,097 | 4/1960 | George | 36/11.5 |
| 2,952,925 | 9/1960 | Held | |
| 3,320,347 | 5/1967 | Greenawalt | |
| 3,398,469 | 8/1968 | Bressan | 36/11.5 |
| 3,470,880 | 10/1969 | Pagliano | |
| 3,596,291 | 8/1971 | Thill | |
| 3,870,145 | 3/1975 | Mizuno | |
| 3,999,311 | 12/1976 | Epstein | |
| 4,020,569 | 5/1977 | Fukuoka | 36/11.5 |
| 4,124,946 | 11/1978 | Tomlin | 36/11.5 |
| 4,279,083 | 7/1981 | Dilg | |
| 4,294,023 | 10/1981 | Banford | 36/11.5 |
| 4,316,333 | 2/1982 | Rothschild | |
| 4,535,554 | 8/1985 | De Obaldia | 36/11.5 |
| 4,694,590 | 9/1987 | Greenawalt | |
| 4,813,162 | 3/1989 | Harris | 36/11.5 |
| 4,928,404 | 5/1990 | Scheuermann | 36/37 |
| 4,955,148 | 9/1990 | Padilla | 36/43 |
| 4,967,750 | 11/1990 | Cherniak | 36/11.5 |
| 5,005,575 | 4/1991 | Geri | 36/43 |
| 5,555,584 | 9/1996 | Moore, III et al. | 36/88 |

*Primary Examiner*—M. D. Patterson
*Attorney, Agent, or Firm*—Henderson & Sturm

[57] ABSTRACT

A custom-made shoe of a sandal-type having a sole, an orthotic unit prescribed specially for the foot of the wearer adhered to the sole a vamp unit secured forwardly to the sole, and a counter secured to and projecting upwardly from the rear periphery of the sole.

2 Claims, 3 Drawing Sheets

5,787,608

1
CUSTOM-MADE FOOTWEAR

TECHNICAL FIELD

The present invention relates generally to footwear and specifically to custom made footwear incorporating orthotics.

BACKGROUND ART

The foot is a highly complex structure, containing 26 bones, 29 joints, and 42 muscles. Some statistics show that in a lifetime, the average individual will walk some 115,000 miles, or more than four times around the world. It is not surprising therefore, that good footwear is one of the most important items of apparel; and when added to millions of people who suffer from orthopedic problems of the foot and spine, that custom footwear is a major means of providing comfort for these and other people.

The use of custom made orthotics—inserts for shoes; orthopedic shoes for helping certain foot problems; shoe modifications in the form of heel build-ups; and rocker-type bottoms for shoes, as examples of solving certain orthopedic problems are well known in this field.

Historically, however, men and women who normally use prescription orthotic devices in their shoes are forced to temporarily give up the corrective or stabilizing orthotics if they want to wear sandals due to the nature and design of the sandals. Ordinary sandals lack the ability to stabilize the heel of a patient's foot because there is typically only a narrow strap that wraps around the ankle. Additionally, if a patient tried to use an orthotic insert with a sandal, the insert would not remain in place because of the sandal's loose fit and open toe, heel and sides. It is to the provision of a solution to this problem that this invention is directed.

DISCLOSURE OF THE INVENTION

The present invention comprises a custom-made sandal that incorporates orthotic elements and heel stabilizers to provide postural support and stability to its wearer.

The custom made orthotic portion of the sandal supports the three arches in the foot; the inner-longitudinal arch (navicular), the outer-longitudinal arch (cuboid), and the anterior transverse arch. Rear-foot posting for pronation or supination is also built into the orthotic design to achieve proper foot posture and balance. Heel spur accommodations as well as a heel lift for an anatomical short leg can be built into the orthotic based on the individual's needs.

The sole, or bottom of the sandal is shaped and sized to fit the foot of the wearer and is made of a thermoplastic rubber material for durability and shock absorption. An intermediate layer of a stiff fiber material is similarly shaped and adhered to the top of the sole. Water resistant sponge rubber supports for the three arches in the foot are formed, located and adhered to the top of the intermediate layer to satisfy the prescribed support needs of the wearer. An open cell polyurethane foam heel pad is also adhered to the top of the intermediate layer for shock protection during the heel strike phase of the gait cycle. A top layer of slip-resistant, black-knobby rubber is then applied over the foot bed to provide a non-slip, foot cushioning surface. The top layer provides water-tight protection to the sandal interior.

Attached to the sole and extending around the heel portion of the sandal approximately one-third its length is a rear-foot support element to control pronation or supination thereby maintaining proper foot posture and balance. The rear-foot support comprises a rigid plastic element that may be covered by neoprene padding and a nylon liner or other suitable material for comfort and durability. Also attached to the sole is a fore-foot strap located on the sandal where the wearer's metatarsal joints will be received. The strap can be made of leather or other suitable material for durability, looks and long wear. The strap utilizes a hook and loop adjustable strapping system for adjustable fit and support. A rear-foot strap is attached to the rear-foot support element, and crosses over the front of the wearer's ankle and utilizes a hook and loop adjustable strapping system for adjustable fit and support. The rear foot strap is made of the same material as the fore-foot strap.

It is an object of this invention to provide a novel footwear that will allow patients/wearers to have orthotic support for all their activities.

It is another object of this invention to provide a novel sandal that will provide postural support, stability and shock absorbing capabilities.

Yet another object of this invention is to provide a custom-made shoe or sandal that provides an exact prescription orthotic support for individuals.

Still another object of this invention is to build custom-made spinal pelvic stabilizers right into attractive, comfortable sandals.

Another object of this invention is to provide to those individuals who require postural support, an enjoyment heretofore missed, that of wearing sandals.

It is another object of this invention to provide a sandal that has a non-slip, foot cushioning surface formed over the orthotic elements, which surface is also water-tight so the sandal can be worn in wet conditions without damaging the orthotic elements.

BRIEF DESCRIPTION OF THE DRAWINGS

These and other attributes of the invention will become more clear upon making a thorough review and study of the following description of a preferred embodiment, particularly when reviewed in conjunction with the drawings, wherein.

BEST MODE FOR CARRYING OUT THE INVENTION

Figure 1:
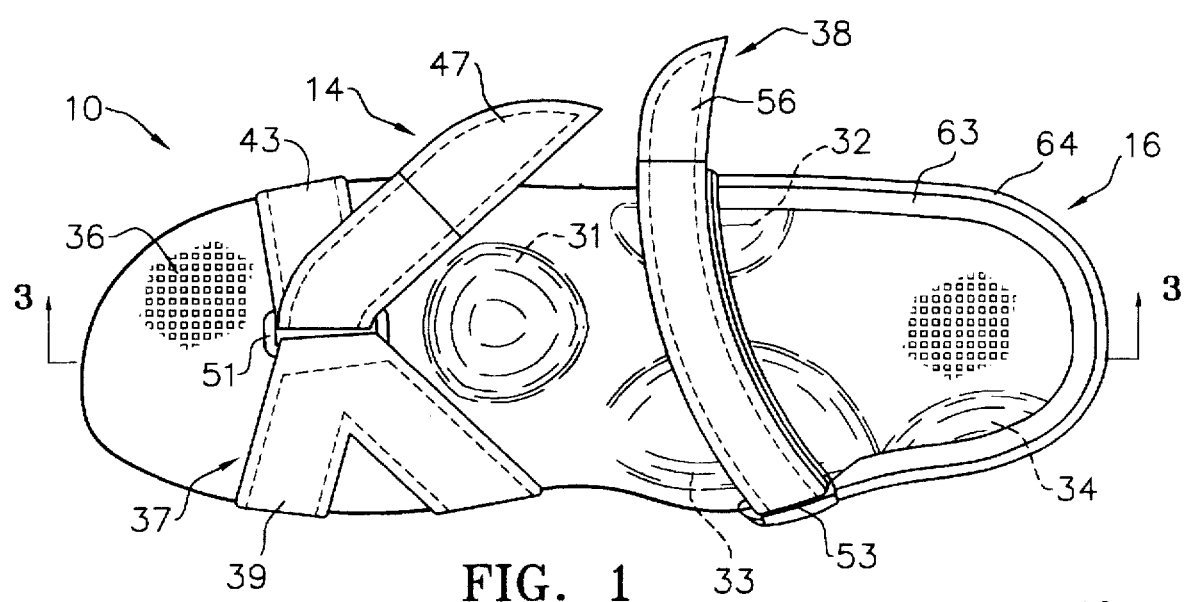
FIG. 1 is a top plan view of a sandal embodying this invention.
Figure 2:
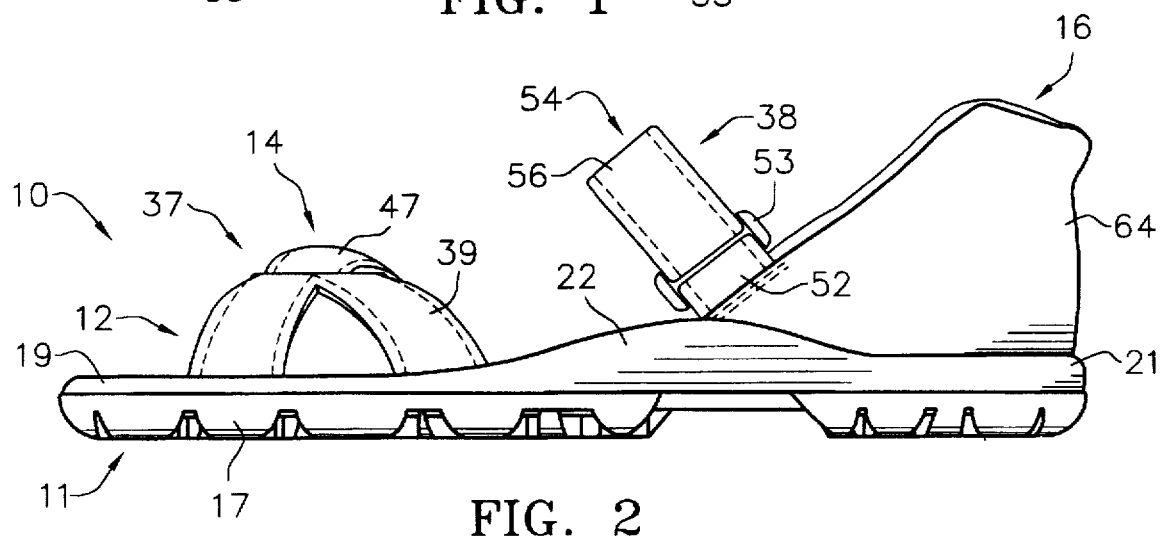
FIG. 2 is a side elevational view of the sandal of FIG. 2.

Referring now to FIG. 1, the embodiment of the invention depicted includes a shoe (10) of the sandal type provided generally with a sole (11), an orthotic unit (12) adhered to the sole (11) and tailored to a particular individual's foot, and including further a shock absorbing heel inset (13), a vamp unit (14) for partially covering a foot (not shown), and a counter (16) projecting upwardly from the rear periphery of the sole (11).

Figure 3:
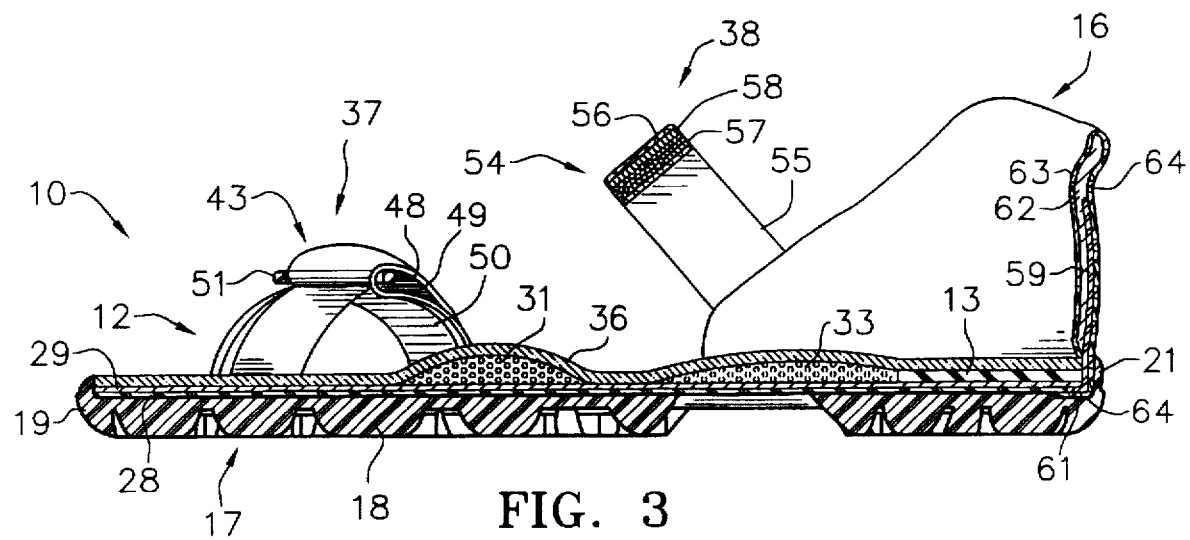
FIG. 3 is a sectional view as taken along the line 3—3 in FIG. 1.
Figure 5:
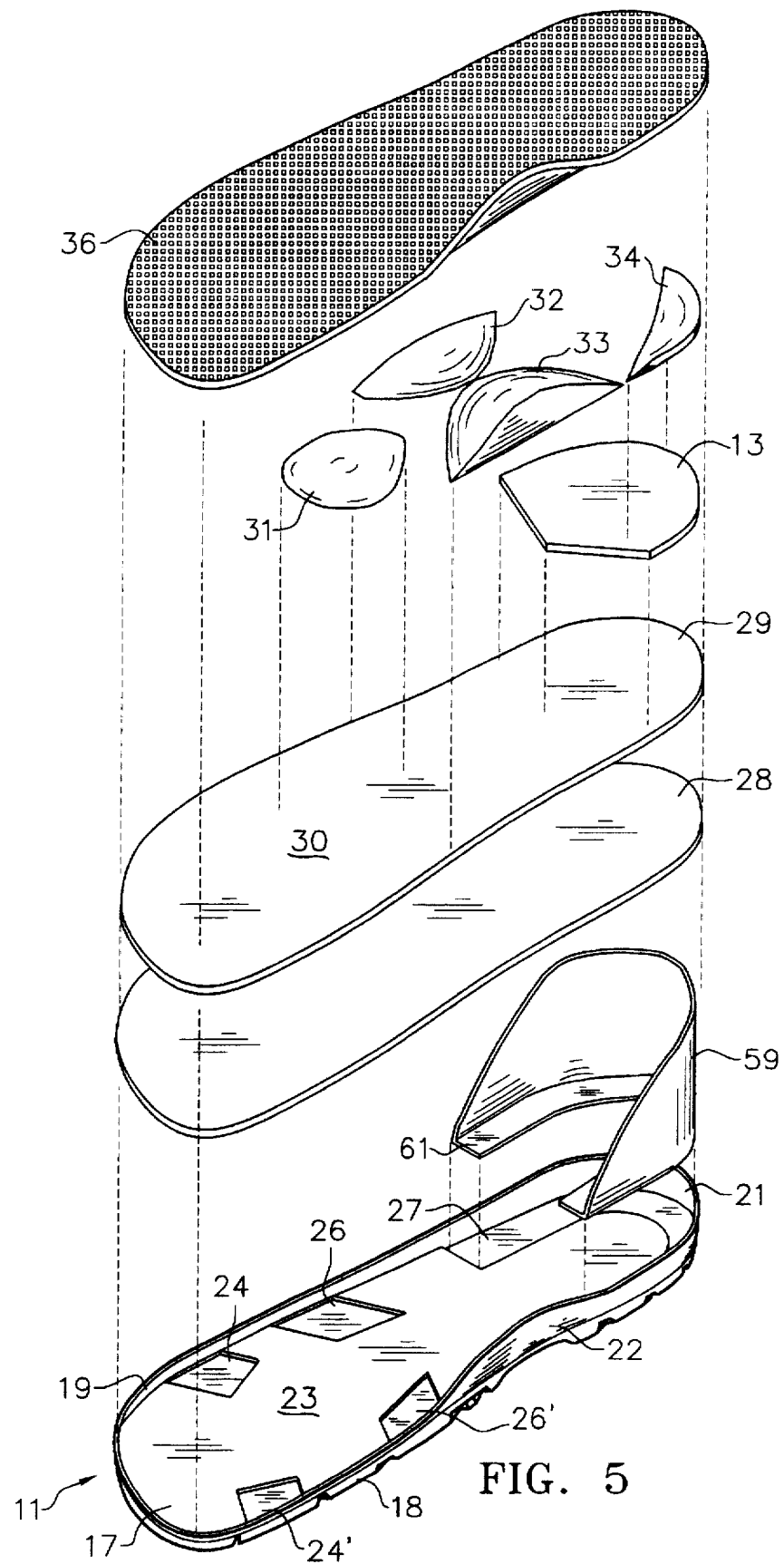
FIG. 5 is an exploded, perspective view of certain parts of this invention.

More particularly, the sole (11) comprises a sole proper (17) of an outline to support the entire foot; of a thickness as predetermined for the use, in this instance with a base (18) of a criss-cross, deeply cut structure of a thermoplastic rubber material (FIG. 3). An upturned lip (19) is formed about the periphery of the sole proper (17), with a higher raised portion (21) (FIG. 5) at the heel area, and an even higher portion (22) for additional support at the instep. The upper face (23) (FIG. 5) of the sole proper (17) has a pair of forward, transversely opposite recesses (24), (24'), a second pair of intermediate, transversely opposite recesses (26), (26') and a U-shaped recess (27) at the rear thereof, all formed in the face (23) for securement with portions of the vamp unit (14) and the counter (16).

The orthotic unit (12) comprises a lower, semi-flexible element (28) and an upper, semi-flexible element (29), both elements (28), (29) having an outline similar to that of the sole proper (17) such as to fit within the lip (19). The elements (28), (29) are of a fiberboard-type material, and can be combined into a single element if desired. Sponge rubber arch support elements (31), (32), (33), (34) (FIG. 5), formed according to prescribed arch support needs of the individual for whom the shoe (10) is custom-made, are adhered to the upper surface (30) (FIG. 3) of the upper element (29) at prescribed locations.

The heel inset (13), made of a polyurethane foam providing a higher degree of shock absorption than the arch support elements (31)–(34), and of a curved shape to fit over the rear portion of the upper element (29), is adhered to the upper element (29) such that the rear, curved peripheries of each mate. It will be noted (FIG. 3) that the heel inset (13) has a thickness similar to the combined thickness of the two elements (28), (29) and is not covered over or placed beneath any of the arch support elements (31)–(34). The elements (31)–(34) and the heel inset (13), along with remaining exposed areas of the upper element surface (30) are covered over by a layer (36) of slip-resistant, knobby rubber material; the layer (36) having an outline similar to that of the upper element (29) and a thickness similar to that of the heel inset (13).

Preparation of the orthotic unit (12) may comprise use by a chiropractor, or other health care professional person skilled in this field and licensed to prescribe orthotics, of a casting kit as described in U.S. Pat. No. 3,320,347 entitled Method of Making an Arch Support by Measuring an Impression of a Foot, issued May 16, 1967 to M. H. Greenawalt, which patent is incorporated herein by reference. Preparation of the orthotic unit (12) may also comprise the use of an electronic casting machine that is capable of sending three dimensional data of the foot to the laboratory for manufacturing purposes. The results of the casting or foot impression mold are then analyzed and a prescription is generated. Other methods of preparation may be utilized, and the invention is not to be limited thereby. These elements (31)–(34) support the three arches of the foot: the inner-longitudinal arch (navicular), the outer-longitudinal arch (cuboid), and the anterior transverse arch. The heel inset (13) is placed into the heel zone of the orthotic unit (12) to absorb shock during the first phase (heel strike) of the gait cycle. Rear foot posting for pronation or supination is built into the orthotic design to achieve proper foot posture and balance. Heel spur accommodations as well as a heel lift for an anatomical short leg can be built into the orthotic based on the individual's specific needs.

Figure 4:
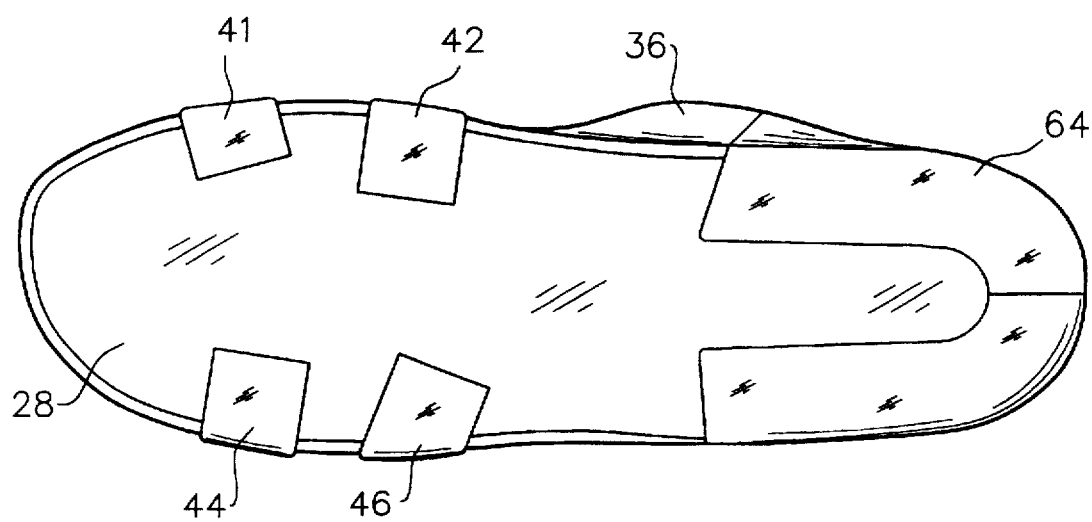
FIG. 4 is a bottom plan view of the shoe of this invention with the sole removed.

The vamp unit (14) (FIGS. 1–4) comprises separate forward and rear vamp portions (37), (38). The forward portion (37) is primarily of a natural suede leather and includes a left V-shaped strap (39) having free ends (41), (42) (FIG. 4), and a right V-shaped strap (43) also having free ends (44), (46) (FIG. 4) and a free securing end (47) (FIG. 1). On its inner surface, the end (47) is provided with an elongated Velcro loop portion (48); and on the outer surface of the right strap leg (50) (FIG. 3), an elongated Velcro hook portion (49) is provided such that upon passing the securing end (47) through a buckle (51) affixed to the left strap (39), the securing end (47) may be adjustably, secured to the right strap leg (50) to properly fit over the foot of the wearer. The free ends (41), (42) of the left strap (39) are affixed, as by glueing or the like around the edges of the elements (28), (29) and beneath same as shown in FIG. 4.

The rear vamp portion (38) is also of a natural suede leather and comprises a loop (52) affixed to the counter (16), with a buckle (53) (FIG. 2) held thereby, and a strap (54) one end (55) (FIG. 3) secured to the counter (16) on a side opposite the loop (52), and the other end (56) free. Elongated portions (57), (58) of Velcro hooks and loops, respectively, are sewn end-to-end along the inner side of the strap (54) such that it may be passed through the buckle (53) and then adjustably folded and held against itself due to the Velcro portions (57), (58), positioning the rear vamp portion (38) comfortably over the instep of the wearer's foot.

Lastly, the counter (16) of the custom-made shoe (10), herein of the sandal-type, comprises a rigid, cup-shaped heel support (59) formed of plastic or other suitable material, and having a lower, U-shaped ledge (61). A cup-shaped padding element (62) (FIG. 3) of neoprene is adhered to the inner surface of the support (59), a liner (63) of a soft material is formed completely about the interior of the element (62) and the remainder of the heel support (59), and a suede leather element (64) is formed completely about the exterior of the heel support (59), including the bottom surface of the ledge (61). The upper edges of the inner liner (63) and the outer suede element (64) are attached, as by stitching, for example, to complete the counter (16). The ledge (61) and element (64) are adhered to the base of element (28) at the heel area thereof (FIG. 4), having a thickness comparable to that of the vamp strap ends (41), (42), (44) and (46).

It should be noted that the orthotic unit (12) including the heel inset (13), the vamp unit (14) and the counter (16) are assembled together as a composite unit, with that composite unit then adhered with the face (45) of the sole proper (17). The glued ends (41), (42), (44) and (46) (FIG. 4) of the straps (39), (43) are fitted into and glued to the respective recesses (24'), (26'), (24), (26) of the sole proper (17). The ledge (61) of the counter (16) with the exterior element (64) are fitted into and adhered to the rear recess (27) (FIG. 5), further support provided by adhering the lower exterior circular portion of the counter (16) to the inner face of the raised portion (21) of the sole proper lip (19) (FIG. 3).

I claim:

1. A footwear construction custom-made for a wearer comprising:

a sole having a forward portion and a heel portion;

an orthotic unit prescribed specially for a foot of the wearer, and adhered to said sole;

a vamp unit secured to said sole adjacent said forward portion;

a counter secured to said heel portion of said sole and projecting upwardly therefrom;

said sole having further an upturned lip formed about the periphery thereof;

said sole having further an upper face, and with a plurality of recesses of predetermined spacing formed within the said upper surface thereof, and wherein one said recess has a U-shape and is formed about said heel portion;

said orthotic unit including further a semi-flexible component having an outline similar to the outline of said sole and placeable onto said sole and within said lip; said orthotic unit component having an upper face and a lower face, and including further a shock absorbing heel inset secured to said component upper face, said inset having a U-shaped semi-circular periphery; and said counter including a rigid cut-shaped element having an inturned lip, said element secured about the periphery of said component with said lip secured to said lower face and nested into said U-shaped recess.

2. A footwear construction custom-made for a wearer comprising:

- a sole having a forward portion and a heel portion;
- an orthotic unit prescribed specially for a foot of the wearer, and adhered to said sole;
- a vamp unit secured to said sole; and
- a counter secured to said heel portion of said sole and projecting upwardly therefrom;
- said vamp unit including a forward vamp portion and a rear vamp portion, said forward vamp portion including left and right V-shaped strap units, said left unit having a pair of legs with outer ends each secured beneath said orthotic unit to said sole, and with inner ends joined together and to which joint a fastener is secured, said right unit having a pair of legs with outer ends each secured beneath said orthotic unit to said sole, and with inner ends free to each pass through said fastener, said right unit legs having respective hook and loop fastener portions affixed thereto on facing surfaces, said outer ends of each left and right units spaced apart to form openings therebetween; and
- said vamp unit including further a strap secured at one end to one side of said counter and an opposite end of said strap operably connected to an opposite side of said counter for extending over the instep of the foot of the wearer.

* * * * *